United States Patent [19]

Ehret et al.

[11] 3,941,487
[45] Mar. 2, 1976

[54] COLORIMETRIC FLUID ANALYZER

[75] Inventors: Robert J. Ehret, Los Altos; Donald E. Stephens, Palo Alto; Douglas H. Durland, Palo Alto; Thomas D. Sharples, Atherton, all of Calif.

[73] Assignee: Beckman Instruments, Inc., Fullerton, Calif.

[22] Filed: Oct. 18, 1974

[21] Appl. No.: 516,008

Related U.S. Application Data

[63] Continuation of Ser. No. 351,431, April 16, 1973, abandoned.

[52] U.S. Cl............... 356/181; 73/23.1; 73/61.1 C; 356/184; 356/206; 356/244; 356/246
[51] Int. Cl.².. G01J 3/46; G01N 21/28; G01N 1/10
[58] Field of Search ....... 356/36, 39, 178, 180, 181, 356/184, 186, 189, 206, 244, 246; 73/23.1, 61.1 C

[56] References Cited
UNITED STATES PATENTS

| | | | |
|---|---|---|---|
| 2,952,762 | 9/1960 | Williams et al. | 219/553 |
| 3,236,602 | 2/1966 | Isreeli | 356/39 |
| 3,284,566 | 11/1966 | James et al. | 350/171 |
| 3,315,229 | 4/1967 | Smithline | 356/36 |
| 3,330,904 | 7/1967 | Gebel | 350/171 |
| 3,497,690 | 2/1970 | Wheeless, Jr. et al. | 356/39 |
| 3,515,491 | 6/1970 | Emary | 356/246 |
| 3,523,737 | 8/1970 | Wood et al. | 356/201 |
| 3,558,892 | 1/1971 | Seeley | 250/205 |
| 3,572,944 | 3/1971 | Hanline et al. | 356/206 |
| 3,657,537 | 4/1972 | Wheless, Jr. et al. | 356/39 |
| 3,663,891 | 5/1972 | Kocher et al. | 356/246 |
| 3,703,336 | 11/1972 | Rosse et al. | 356/205 |
| 3,751,173 | 8/1973 | Sanz et al. | 356/246 |

OTHER PUBLICATIONS

Jenkins & White; Fundamentals of Optics; McGraw Hill; 3rd ed., 1957, (New York); p. 432.

*Primary Examiner*—Vincent P. McGraw
*Attorney, Agent, or Firm*—R. J. Steinmeyer; F. L. Mehlhoff

[57] ABSTRACT

A light beam is passed through a cuvette, through which flows liquid to be analyzed optically for concentration of color reacted amino acids. The emergent beam is directed through a series of dichroic beam separators and pass band filters to produce three beams of substantially three different wavelengths. Photoelectric detectors produce electrical signals corresponding to each of the three wavelengths. Two of the signals are characteristic of the substance to be detected. The third is subtracted from the other two wavelength signals to produce a pair of output signals from which base line noise has been substantially eliminated.

20 Claims, 12 Drawing Figures

COLORIMETRIC FLUID ANALYZER

This is a continuation of application Ser. No. 351,431 filed Apr. 16, 1973, and now abandoned.

BACKGROUND OF THE INVENTION

Transparent and translucent samples have been analyzed by means of colorimeters or spectrophotometers which ascertain absorbance and/or transmittance at various wavelengths of the sample. Liquids and substances, which are capable of being dissolved or carried in suitable liquids, may be analyzed by passing the liquid through a cuvette which is mounted in the path of a light beam of a colorimeter. In order that analyses may be accomplished quickly, it is desirable, in the case of fluid analysis, to provide means for making continuous indications of the absorbance or transmittance at various wavelengths of light through the sample as the liquid flows through the cuvette. In the case of amino acid analysis, for example, the effluent from a liquid chromotograph instrument, where the amino acids are separated, is carried by the buffer solution into a mixing chamber or tube where a ninhydrin solution is introduced. The amino acid sample, buffer solution and ninhydrin are heated to bring out the color characteristics. The reacted effluent, carrying the separated amino acids, is then caused to flow through the cuvette of a colorimeter.

The analysis in the cuvette is accomplished by ascertaining the transmittance or absorbance at three different wavelengths such as 440 millimicrons, 570 millimicrons and 690 millimicrons. However, in the past, when making analyses of this type for the analysis of amino acids and also for similar colorimetric analyses of other liquids, it has been necessary to make separate determinations for the different wavelengths or to use separate cuvettes with separate colorimeters and this has required redundancy of apparatus greatly increasing the expense and complicating the operation of the apparatus.

It is an object of the invention to provide a colorimeter suitable for use in the analysis of amino acids which employs a single cuvette.

It is also an object to overcome the effect of base line noise or changes in base line caused by variations in flow rate, particulate matter in the cuvette, variations in metering rate, etc.

It is another object of the invention to provide absorbance signals as contrasted with transmittance signals in order to permit the signals to be ranged electrically on a recoder utilizing a simple "universal" linear scale. Thus, it is an object of the invention to avoid the necessity for employing multiple cuvette systems with long and short path lengths to achieve differing scale ranges.

A further object of the invention is to provide optical systems which permit the use of small volume cuvettes with diameters as low as 0.030 inches and relatively long path lengths through optimized collection and conservation of the shorter wavelength radiations passing from the source through the cuvette.

Other and further objects, features and advantages will become apparent as the description proceeds.

SUMMARY OF THE INVENTION

In carrying out the invention in accordance with a preferred from thereof, especially as applied to the analysis of amino acids which have been treated to bring out the color characteristics of a flowing fluid effluent, a single cuvette is provided through which flows the fluid stream to be analyzed. The cuvette is placed in the optical path of a photometer which analyzes the flowing stream from a liquid chromotograph instrument at three distinct wavelength bands. Individual output signals, each continuous, are produced for recording or other processing. The output signals are linear in optical absorbance units with multiple ranging from full scale of 0.1 absorbance units to 2.0 absorbance units thereby permitting use with simplified linear scale recorders and automatic integrators.

A unique optical and electronic arrangement is utilized which provides two-channel/dual-wavelength per channel operation. The optical arrangement effects a large reduction in analyzer base line noise and extends the basic sensitivity capability of the chromotographic analyzer.

An incandescent light source is employed to pass a light beam through the cuvette carrying the sample. The beam emerging from the sample is separated into several different light beams, each containing luminous energy within a relatively narrow band of wavelengths. In the case of an amino acid analyzer, two beams are produced having wavelengths centered in one case on 440 millimicrons and in the other case on 570 millimicrons. A third light beam is produced in which the wavelengths are centered on 690 millimicrons. This third beam is employed to produce an optical absorbance signal representative of system noise which is subtracted from the signals representing optical absorbances of the other two light beams.

The wavelength separation is accomplished by the use of dichroic mirrors and interference filters, that is filters which pass only narrow bands of wavelengths. The first dichroic mirror is provided with a suitable coating so that it reflects approximately 98% of the light impinging thereon in the range of wavelengths to approximately 520 millimicrons and transmits the remaining luminous energy. The transmitted beam, containing the remaining luminous energy above approximately 520 millimicrons, is projected to a second dichroic mirror which has a coating serving to reflect 98% of the luminous energy up to approximately 635 millimicrons and to transmit the remaining luminous energy. The first reflected beam is projected through a narrow band interference filter which has a band width, at half peak height, of approximately 19 millimicrons centered on 440 millimicrons and thence projected onto a photoelectric detector, which produces an electrical signal representative of the transmittance through the curvette of 440 millimicron light. In a similar manner, the second reflected beam is transmitted through a filter of the interference type passing a narrow band of wavelengths, at half peak height, of approximately 8.5 millimicrons in width centered upon 570 millimicrons wavelength and finally projected to a photoelectric detector which produces an electrical signal representative of transmittance at 570 millimicrons.

The light beam transmitted through the second dichroic mirror is projected through a third narrow band interference filter of approximately 10 millimicrons bandwidth at half peak height centered on 690 millimicrons and thence projected onto a third photoelectric detector to produce a signal representative of sample transmittance at 690 millimicrons.

Preferably, the three electrical signals are amplified. Then each of the three amplified signals is supplied to converting means, including logarithmic type operational amplifier, which invert the signals to produce signals representative of absorbance at the wavelength in question instead of transmittance. The converting means then produces output signals representative of the difference between the optical absorbances between the 440 millimicron signal and the 690 millimicron signal and between the 570 millimicron signal and the 690 millimicron signal. Since the 690 millimicron signal is a signal representative of those inputs in the cuvette which contribute to base line noise, the subtraction of this optical absorbance signal has the effect of substantially reducing base line noise in the output signals.

Thence the outputs representative of the 440 minus 690 millimicron and the 570 minus 690 millimicron wavelength bands are supplied to a ranging and channel selection unit with outputs to recorders or to other signal processing apparatus. In some instances it is desirable to provide a summation amplifier which produces a signal representing the sum of the outputs of the 440 minus 690 millimicron and 570 minus 690 millimicron signals. The output of the summing amplifier is also supplied to the ranging and channel selection unit so that this additional information may be recorded for analysis of the sample.

Preferably means are also provided for achieving substantially uniform temperature of the optical head and the sample flowing through the cuvette. This is accomplished by providing an input field line with a coil thermally lagged to the optical head so that the fluid and the optical head reach a uniform temperature.

It has also been found that the light energy output of the light source reduces as the temperature of the device increases. Accordingly, a lamp housing for the light source is provided which has a temperature sensing device, such as a thermistor, lagged to it which, in turn, is connected to a power input control circuit of the lamp so as to increase or reduce the power to the lamp as the temperature rises or falls thereby achieving substantially uniform light output independent of variations in ambient temperature.

A better understanding of the invention will be afforded by the following detailed description considered in conjunction with the accompanying drawing.

DRAWINGS

FIGS. 10, 10A and 10B, together, are a circuit diagram of electronic circuits of the apparatus.

Like reference characters are utilized throughout the drawing to designate like parts.

DETAILED DESCRIPTION

Figure 1:
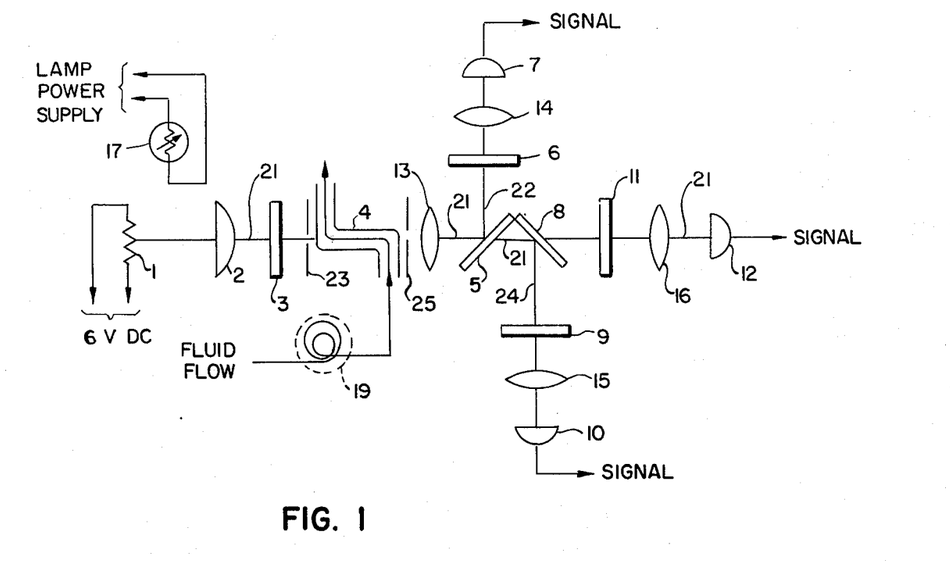
FIG. 1 is a schematic diagram of the optical elements in an embodiment of the invention.

As shown in FIG. 1, the optical head employs a lamp 1 represented in the drawing by a filament connected to a 6-volt direct-current source of power. The lamp 1 is preferably a tungsten lamp of the quartz iodine type supplying visible light which is collected by an aspheric condensing lens 2. There is an infrared absorbing filter 3 interposed in the optical path from the condensing lens 2 with a curvette 4 mounted in the optical path beyond the infrared absorbing filter 3. Apertures 23 and 25 with diameters slightly less than the cuvette bore are provided to restrict the transmitted illumination to the liquid within the cuvette 4. Lens 13, at its focal distance from aperture 25, collimates the light beam for passage through the remainder of the system.

To maximize the energy, a dichroic mirror 5 preferentially reflects wavelengths shorter than approximately 520 millimicrons, with 98% minimum efficiency at 440 millimicrons, onto narrow band interference filter 6. For amino acid analysis, using ninhydrin color reaction, filter 6 has 50% transmission centered at 440 millimicrons with a half peak width not greater than 19 millimicrons. A lens 14 concentrates the light passing through the filter 6 onto a photoelectric receiver, such as a photo diode, 7. Light above 520 millimicrons is transmitted through mirror 5 along the original light path.

A second dichroic mirror 8 preferentially reflects wavelengths shorter than approximately 630 millimicrons, with 98% minimum efficiency at 570 millimicrons, onto narrow band interference filter 9. For amino acid analysis, using ninhydrin color reaction, filter 9 has a 50% transmission centered at 570 millimicrons and a half height band width of 8.5 millimicrons. Lens 15 concentrates the light on photoelectric receiver 10.

The remainder of the light, not reflected by dichroic mirrors 5 or 8, consisting of at least 70% of the visible light of wavelength greater than 630 millimicrons continues along the first path and falls on narrow band interference filter 11. Filter 11 has a 50% transmission centered at 690 millimicrons and a half height bandwidth of 10 millimicron. Lens 16 concentrates the beam on photoelectric receiver 12.

Because the output of the lamp is sensitive to ambient temperature, means are preferably provided for maintaining the filament of the lamp 1 at a constant color temperature. This may take the form of a temperature sensing device, such as a thermistor 17, which is connected in the circuit of the lamp power supply.

The long path length of the curvette 4 induces a significant sensitivity of the instrument to variations in refractive index of the flowing liquid, such as are due to slight temperature differences between the cuvette and the entering liquid steam. In order to alleviate, as much as possible, differences in temperature between the cuvette 4 and the entering liquid, a coil 19 receiving the fluid before it enters the cuvette 4 is preferably mounted in intimate contact with the optical head. This tends to bring the liquid to the temperature of the optical housing which, of course, is approximately the same as the cuvette.

From FIG. 1 it will be observed that the light, projected from the lamp 1 through the condensing lens 2, the infrared absorbing filter 3, cuvette 4 and the focusing lens 13 along a first optical path, 21, has a portion below a selected wavelength reflected by the dichroic mirror 5 along a second optical path 22 and the remainder thereof transmitted along the main or original optical path 21. A portion of the remaining light below a selected wavelength which travels along the optical path 21 in turn is reflected by the dichroic mirror 8 along a third optical path 24 and the remainder again transmitted through the mirror 8 along optical path 21. The photoresponsive detectors 7, 10 and 12 are thus in the second, third and first optical paths 22, 24 and 21, respectively, as a result of the action of the dichroic mirrors 5 and 8.

The use of the infrared absorbing filter 3 eliminates the longitudinal heat gradient caused by infrared absorption by the liquid in the cuvette 4. In addition, the stream entering the cuvette 4 is maintained in thermal equilibrium with the mass of the photometer owing to the presence of the coil 19 thermally lagged to the body of the optical head. Also, slight changes in the spectral output of the light source 1 with variations in ambient temperature are avoided by compensation of voltage to the lamp 1.

Figure 2:
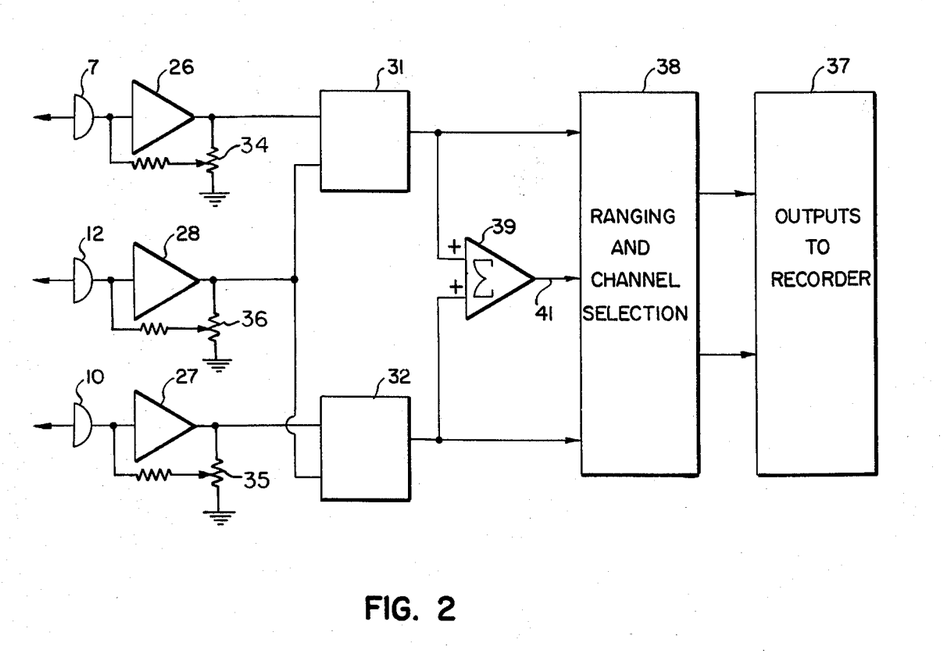
FIG. 2 is a block diagram of electronic elements employed to convert electrical signals representative of optical outputs of the optical apparatus at various wavelengths into useful form for accomplishing analysis and recording to the information.

Electronic circuitry is represented schematically in FIG. 2. Preferably the output signals from the photoelectric detectors 7, 10 and 12 are supplied to buffer amplifiers 26, 27 and 28, respectively. The outputs of the amplifiers 26, 27 and 28 vary linearly with the transmittance of light through the cuvette 4 at the wavelengths 440, 570 and 690 millimicrons respectively. Preferably, however, these signals are converted into signals proportional to absorbance at the wavelengths in question. This is accomplished by suitable means represented in the drawing by converting means 31 and 32, which include logarithmic operational amplifiers 31a and 32a (see FIG. 10A) having inverting input terminals connected to the outputs of buffer amplifiers 26, 27 and 28, respectively. The converting means 31 receives the 440 and 690 millimicron signals and converting means 32 receives the 570 and 690 millimicron signals. The logarithmic operational amplifiers of converting means 31 and 32 are designed so as to compare the signals from the 440 wavelength detector 7 with the 690 signal from the detectors 12 and, similarly the 570 signal with the 690 signal. The converting means produce outputs which are equal to the optical absorbances of the 440 minus the 690 signal and the 570 minus the 690 signal. In order that adjustments of the base line may be made, potentiometers 34 and 35 are interposed in the feedback circuits of amplifiers 26 and 27 (schematically illustrated in FIG. 2 and shown in the circuit of FIG. 10). A similar ranging feedback adjustment 36 (located internally) is provided for the 690 millimicron signal.

A recorder 37 may be provided which receives signals from the outputs of the converting means 31 and 32. For ranging and channel selection, a unit or selector circuitry 38 may be interposed between the converting means 31 and 32 and the recorder 37. As shown, a summation device or summing amplifier 39 may be provided having input terminals also connected to the outputs of the converting means 31 and 32 and having an output line 41 also supplied to the ranging and channel selection unit 38. The selector 38 includes suitable selector switches so that pens in the recorder 37 may record the signals which correspond to absorbance at 440 minus 690 millimicrons and 570 minus 690 millimicrons or, alternatively, may record a single signal representing the sum of the absorbances at 440 minus 690 and 570 minus 690 millimicrons. This is accomplished by connecting the output of the summing amplifier 39 through line 41 instead of the outputs of converting means 31 and 32 to the recorder 37.

Figure 3:
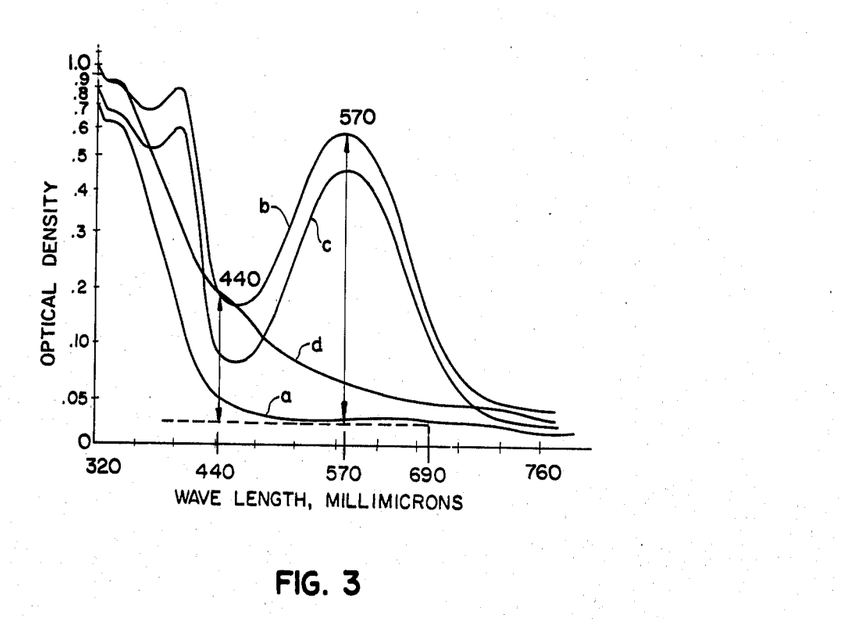
FIG. 3 is a graph illustrating the optical density properties of various specimens including specimens of ninhydrin reacted amino acids and a blank specimen for comparison in which the optical density at various wavelengths is plotted along the ordinate against wavelengths plotted along the abscissa.

The graph of FIG. 3 is introduced to illustrate the advantage of utilizing the selected wavelengths of 440, 570 and 690 millimicron for amino acid analysis in the instance of the use of the ninhydrin color reaction. It will be understood by those familiar with amino acid analysis by column chromatography that the buffer plus ninhydrin in fixed ratio is flowing through the cuvette at a more or less constant rate and, in the absence of an amino acid, the absorbance of this mixture forms the base line (curve *a*) output from the photometer. The segments of amino acids (curves *a*, *b* and *c*), which react with the ninhydrin to give the characteristic color, are required to be detected and quantitized by the photometer. It will be noted that the absorbances due to color (curves *b* and *c*) are relatively very small at 690 millimicrons which is used as the reference for nulling variations due to stream pulsation, vibration of the lamp filament, particles passing through the cuvettes and so on. It will also be noted that the absorbance due to color at 570 millimicrons is quite strong and while that at 440 (curve *d*) is, though far from the peak at 410, quite significantly above base line (curve *a*). Position 440 is used rather than 410 because of the very strong absorbance of the buffer unreacted ninhydrin mixture. That is, the spectral absorbance of the "blank" ninhydrin-buffer solution is shown as curve *a* in FIG. 3. The spectral absorbance of three major groups of ninhydrin reacted amino acids are shown as curves *b*, *c*, and *d*. It will be noted that the absorbances of curve *a* is relatively flat throughout the spectrum from 440 millimicrons to 690 millimicrons; also the absorbance of curves *b*, *c*, and *d* are relatively close to that of curve *a* at 690 millimicrons. By selecting 690 millimicrons as a reference, variations in base line caused by stream pulsations, reagent metering variations, or particulate matter passing through the curvette may then be largely eliminated. It will also be noted that analyzing the contents of the curvette for optical absorbance at 570 millimicrons referred to 690 millimicrons will net the maximum signal for those ninhydrin reacted amino acids included in curves *b* and *c*. For curve *d*, the shoulder at 440 millimicrons provides an absorbance maximum that may still be referred to the 690 millimicron reference, even though the absorption of the "blank" (curve A) is beginning to rise slightly above the 690 millimicron value. By electrically subtracting the absorbance at 690 from that at 440 and 570 base line noise is very largely eliminated.

Figure 5:
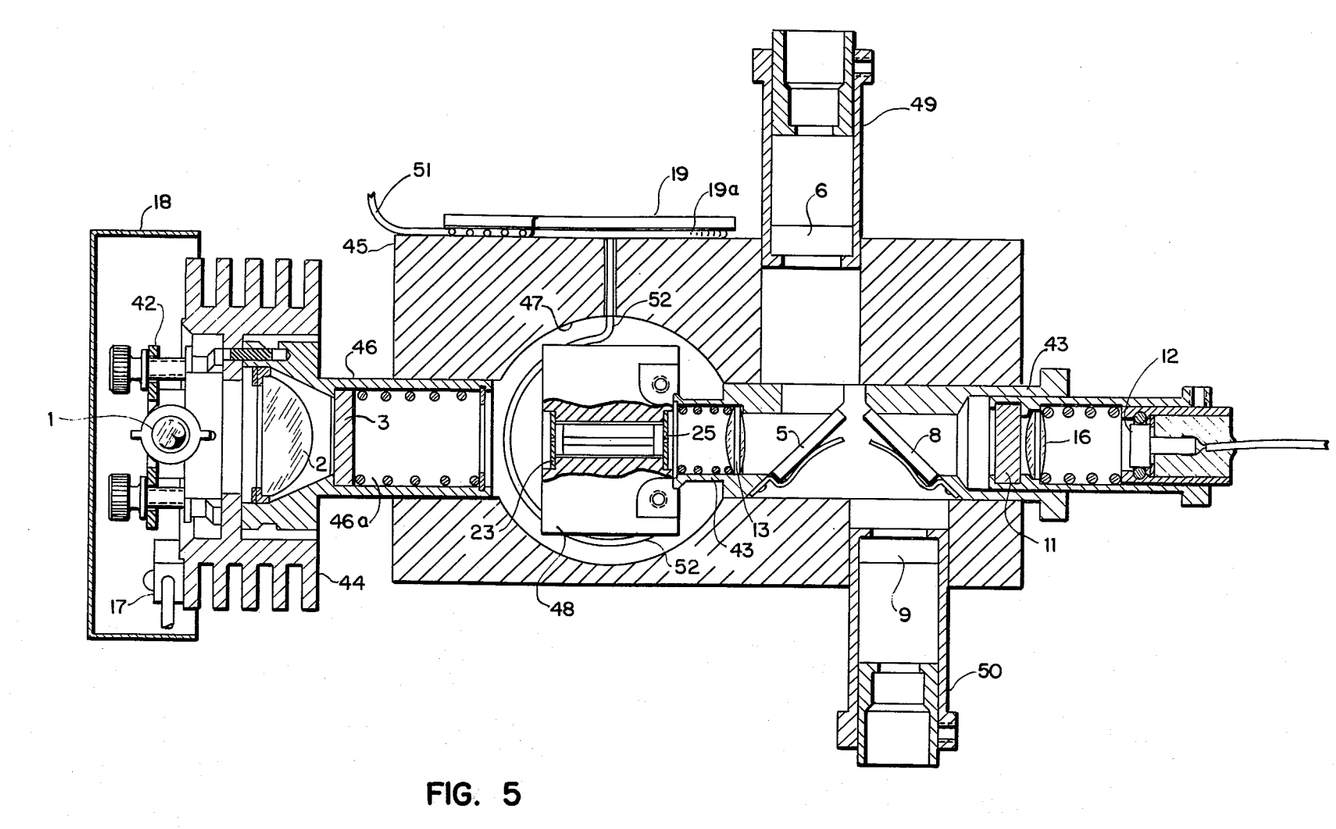
FIG. 5 is a plan view partially in cross-section illustrating an embodiment of the optical head employed in the embodiment of FIGS. 1, 2, and 3 and illustrating the location of the curvette holder.
Figure 6:
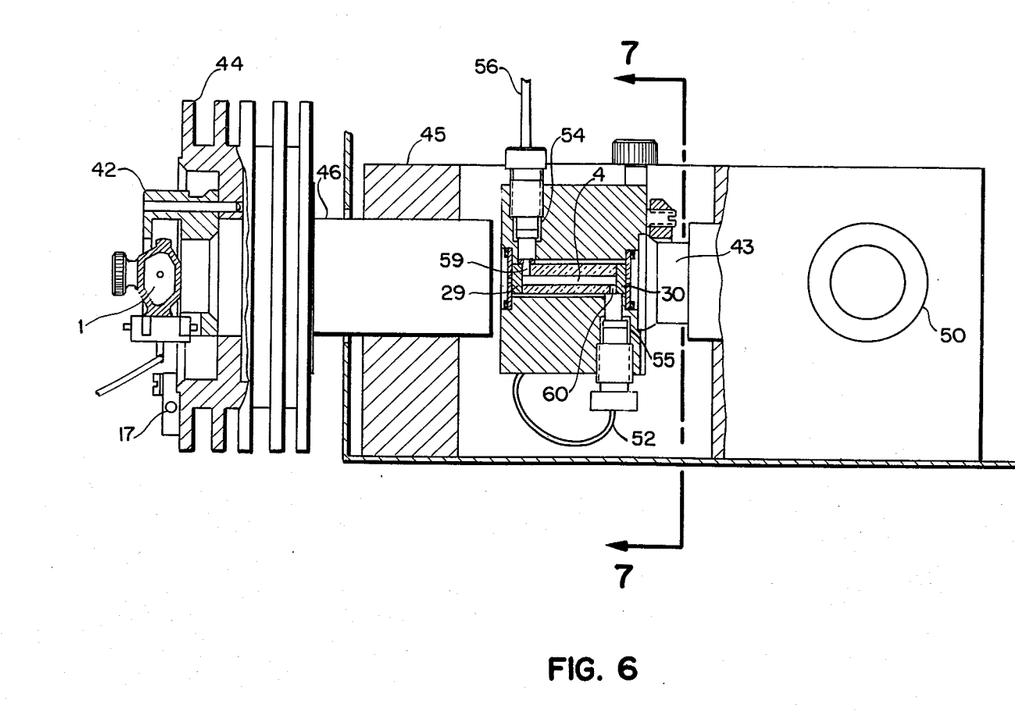
FIG. 6 is a side elevation view taken partially in cross section of the optical head shown in FIG. 5.

The physical structure of the colorimeter is illustrated in FIGS. 5 and 6. There is a lamp holder 42, adjustably mounted in finned housing 44, in turn adjustably mounted on optical tube 46. Removably cover 18 provides protection from air drafts and from accidental burn hazard to personnel. By using relatively low conductivity material such as stainless steel for the tube 46, conduction of heat to the main body 45 in turn minimizing heating of the cuvette and the optical and electro optical elements. Thus, the tube 46 serves not only as a mount for the light source but also holds the aspheric condensor lens 2 and provides a high resistance thermal path between the lamp housing 42 and the optical housing 45. Moreover, the tube 46 carries an infrared heat absorbing filter 3 mounted inside the tube well 46a and removed from the focal point of the aspheric condensor lens 2. There is a cavity 47 in the optical housing 45 which provides clearance for mounting a cuvette holder 48 on the tubular piece 43 which also serves as a mirror mount, relay end holder and cuvette holder mount. The dichroic mirrors 5 and 8 are mounted within the piece 43 in the optical line of sight through the aspheric condensor lens 2, the heat absorbing filter 3, the aperture 23, the cuvette 4, the aperture 25, the relay lens 13, the interference filter 11 for the 690 millimicron beam, the collector lens 16 and the photoelectric detector 12 for the 690 millimicron beam.

Optical tubes 49 and 50 are mounted laterally in the optical housing 45 to enclose light paths from the reflecting surface of the mirror 5 to the photoelectric detector 7 (not shown in FIG. 5) and from the reflective surface of the dichroic mirror 8 to the photoelectric detector 10 (not shown in FIG. 5) for the 440 and 570 millimicron signals, respectively. The optical tubes 49 and 50 as well as optical tube 51 are not shown seated in their mounting aperture in order to illustrate the flexibility available by this arrangement for mounting these members. Set screws (not shown) through the optical housing provide means for securing optical tubes 49, 50 and 51 in place.

As shown in FIGS. 5 and 6, the thermistor 17 or other suitable temperature sensing device for controlling the output of the lamp 1 is mounted on the heat dissipating fin structure 44 in order to respond to the temperature surrounding the lamp 1.

Figure 4:
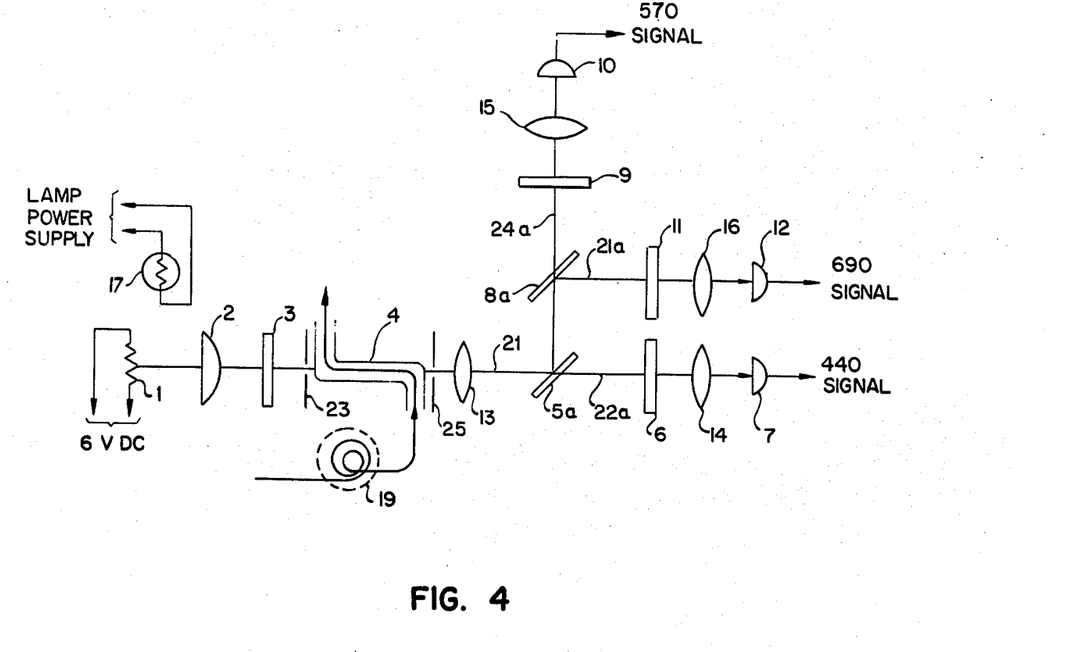
FIG. 4 is a schematic diagram of the optical elements arranged in another embodiment of the invention.

Excellent results have been obtained utilizing the optical arrangement illustrated in FIGS. 1, 5 and 6. It will be understood, however, that the invention is not limited to this precise optical arrangement and that satisfactory results may be obtained also be rearranged optical structure. For example, as illustrated in FIG. 4, the dichroic mirrors may be of a type which transmit the greater portion of the light in wavelengths up to a predetermined or selected maximum wavelength and reflect the balance of the luminous energy. Thus, in the case of FIG. 4 the dichroic mirror 5a transmits approximately 80% of the light wavelengths up to 440 millimicrons and somewhat beyond while reflecting light above approximately 440 millimicrons along the light path 24a. The transmitted energy, including 440 millimicron light, passes along the light path 22a. Then, the dichroic mirror 8a tramsits approximately 85% of the luminous energy up to 570 millimicrons and somewhat beyond along the light path 24a and reflects the remaining luminous energy along the light path 21a. In this embodiment, the 440 millimicron photo-optical detector 7 is mounted in the direct line of the optical path from the condensing lens 2. The dichroic mirror 8a is mounted at one side of mirror 5a in light path 24a extending transversely from the optical housing to the photoelectric detector 10 which will again receive the 570 millimicron signal. Then the filter 11, collecting lens 16 and 690 millimicron photoelectric detector 12 are mounted in the optical path 21a which is, in part, parallel to the optical path 22a.

It will be seen from FIG. 4 that visible light from the lamp 1 collected by the aspheric condensing lens 2 passes through the infrared absorbing filter 3 and through the aperture 23. Consequently, the energy incident upon the cuvette 4 is limited very nearly to the visible spectrum. Liquid flowing through the cuvette 4 absorbs light energy in proportion to the concentration of material in the stream being analyzed. The beam leaving the cuvette 4, passes through aperture 25, through relay lens 13, falls upon the dichroic mirror 5a which transmits incident radiation of wavelengths up to 440 millimicrons and somwhat beyond along the optical path 22a and reflects the longer wavelengths along the optical path toward mirror 8a. The light in this transverse beam impinges on the mirror 8a and the incident light in wavelengths up to 570 millimicrons and somewhat beyond is transmitted along the light path 24a and the longer wavelengths are reflected along the light path 22a. Since filters 6, 9 and 11 are interposed in the light paths 22a, 24a and 21a, the emergent beams are in narrow bands of 440 millimicrons, 570 millimicrons and 690 millimicrons, respectively, impinging upon the corresponding photoelectric detectors 7, 10 and 12, respectively. The outputs of the detectors 7, 10 and 12 are directly proportional to the transmittance at the three different wavelengths and are utilized to produce amplified proportional signals in the amplifiers 26, 27 and 28 (see FIG. 2) respectively. The transmittance proportional signals are converted to absorbance signals in the converting means 31 and 32 so that the recorder 37 may be calibrated in terms of absorbance.

As represented in section in FIG. 5, the temperature equalizing coil 19 is in a pancake spiral form and is clamped in a suitable manner by a holder 19a against the optical housing block 45. Inlet tube 51 is at outside of spiral while outlet tube 52, at center of spiral passes through block 45 and connects to bottom inlet of cuvette 4 (see FIG. 6).

Figure 9:
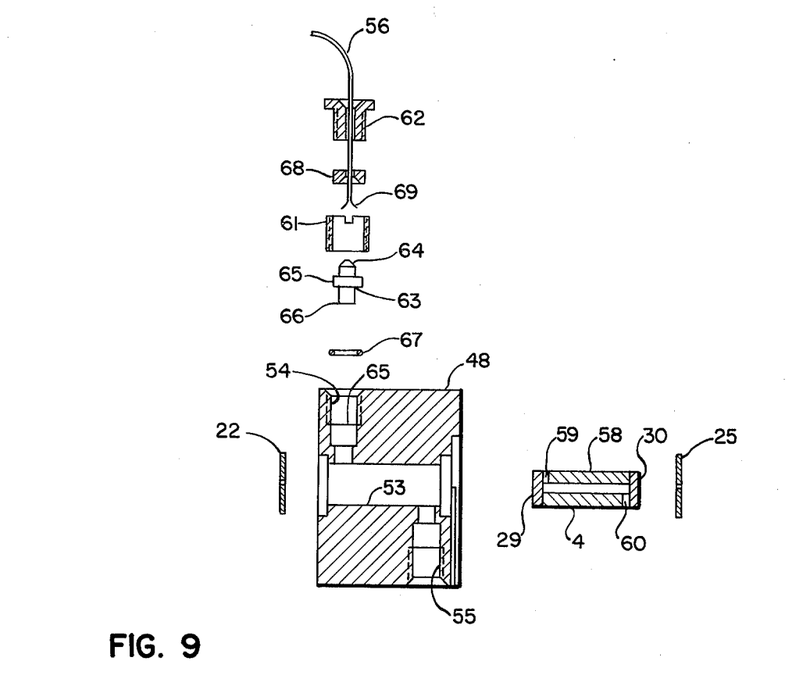
FIG. 9 is an exploded view, in cross section, of the cuvette holder and cuvette assembly employed in the embodiment of the apparatus illustrated in FIGS. 5 and 6.

The manner in which the cuvette 4 is mounted in a cuvette holder 48 is illustrated in greater detail in FIG. 9. As best seen in FIG. 9, the cuvette holder 48 is in the form of a cylinder having a bore 53 to receive the cuvette. The cuvette holder 48 also has lateral bores 54 and 55. The bore 55 is at the inlet end and is adapted to receive means for making connections with tubing 52 (see FIG. 6) from the temperature equilibrating coil 19 through which the fluid to be analyzed is supplied. The bore 54 is at the opposite end and is adapted to receive means for making connections, as shown, to the outlet tubing 56 which exits from the colorimeter and may go to a waste receiver.

As shown in FIG. 9, the cuvette 4 comprises a length of tubing 58 with lateral grooves 59 and 60 at right angles on the opposite ends thereof. The groove 59, in cooperation with optical window 29, forms a passage adapted to communicate with tubing 56 and, similarly, groove 60 with optical window 30 form a passage leading to tube 52. The tube 58 and windows 29 and 30 may be composed of any suitable material such as glass or fused quartz. Window pieces 29 and 30 are fused to the ends of tube 58. It will be observed from FIGS. 5 and 6 that the main portion of the tube 58 extends longitudinally within the holder 48 in the optical axis of the optical housing 45 so that it will have the maximum absorbance effect upon the light beam traveling along the optical axis of the apparatus from the lamp 1.

The upper portion of the bore 54 is threaded to receive an externally threaded bushing 61 and a packing nut 62. There is a hollow fitting 63 having a concical upper end 64, a collar 65 and a lower end 66. The lower end 66 of the fitting 63 is adapted to press an O-ring 67 against the upper surface of the cuvette 4 forming a connection with the lateral outlet passage, formed by groove 59 and window 29 of the cuvette, for sealing the fitting 63 to the outlet end of the cuvette. The bushing 61 is adapted to bear against the shoulder 65 to hold the fitting 63 in place in the bore 54 and maintain compression on the O-ring 67 to seal with the cuvette 4. In order to facilitate sealing, the upper and lower surfaces of the tube 58 are ground flat to provide a convenient sealing surface for the "O" ring 67.

For connecting the outlet tube 56 to the conical portion 64 of the fitting 63 a ferrule 68 is provided and the lower end 69 of the tube 56 is flared. It will be understood that the tube 56 is inserted through the hollow packing nut 62 and the ferrule 68 before the end 69 is flared. After the end 69 has been flared it is sealed to the conical surface 64 of the fitting 63 by means of the packing nut 62 which presses the ferrule 68 against the flared end 69 which, in turn, is pressed against the conical surface 64. Similar connecting means (not shown) are provided in the bore 55 of the cuvette holder 58 for retaining inlet tubing 52 from the coil 19.

Figure 7:
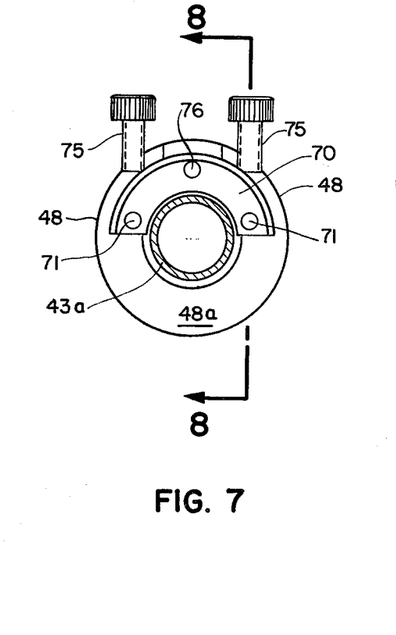
FIG. 7 is an elevation of the cuvette holder and mounting yoke as employed in FIGS. 5 and 6 taken along line 7—7 of FIG. 6.
Figure 8:
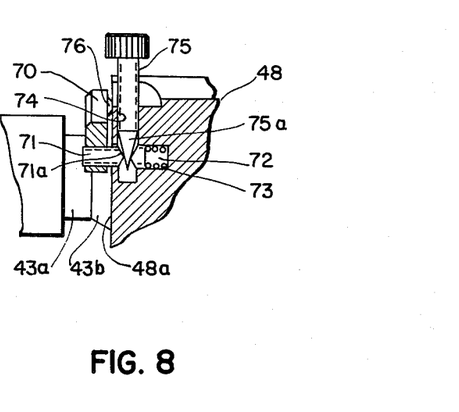
FIG. 8 is a partial view of the optical head and curvette taken along line 8—8 of FIG. 7 illustrating the manner in which the collar supports the cuvette within the cavity of the optical housing.

As will be noted in FIGS. 5, 7 and 8, the cuvette 4 and its holder 48 are supported on the end 43a of the mirror support piece 43 which extends into the cavity 47. The end 43a is provided with a frusto-conical spigot 43b which fits beneath a semicircular clamping collar 70 attached to one end of the cuvette holder 48. Collar 70 is supported on the holder by a pair of draw bars 71, threaded into the collar 70 and extending into smooth bores 72 in the cuvette holder 48. A restoring spring 73 tends to force the draw bars out of the smooth bores 72. Through a threaded opening 74, formed substantially normal to each of the smooth bores 72, is inserted a conical pointed actuating screw 75, the conical point 75a extends into beveled hole 71a formed in the draw bar 71. When threaded screw 75 is turned down into the threaded opening 74 the pointed end 75a pulls the draw bars 71 into the smooth bore 72 and draws the end or seating surface 48a of the cuvette holder 48 up tight against the frusto-conical spigot 43b. In order to make accurate adjustment of the position of the collar 70 to assure a tight fit against the spigot 43b the draw bars 71 may be screwed inwardly or outwardly within the threaded holes of the collar 70. A counter force screw 76 abuts against the upper surface of cuvette holder 48 and serves to retain a uniform space between the collar and the end surface 48a of the holder 48.

Figure 10:
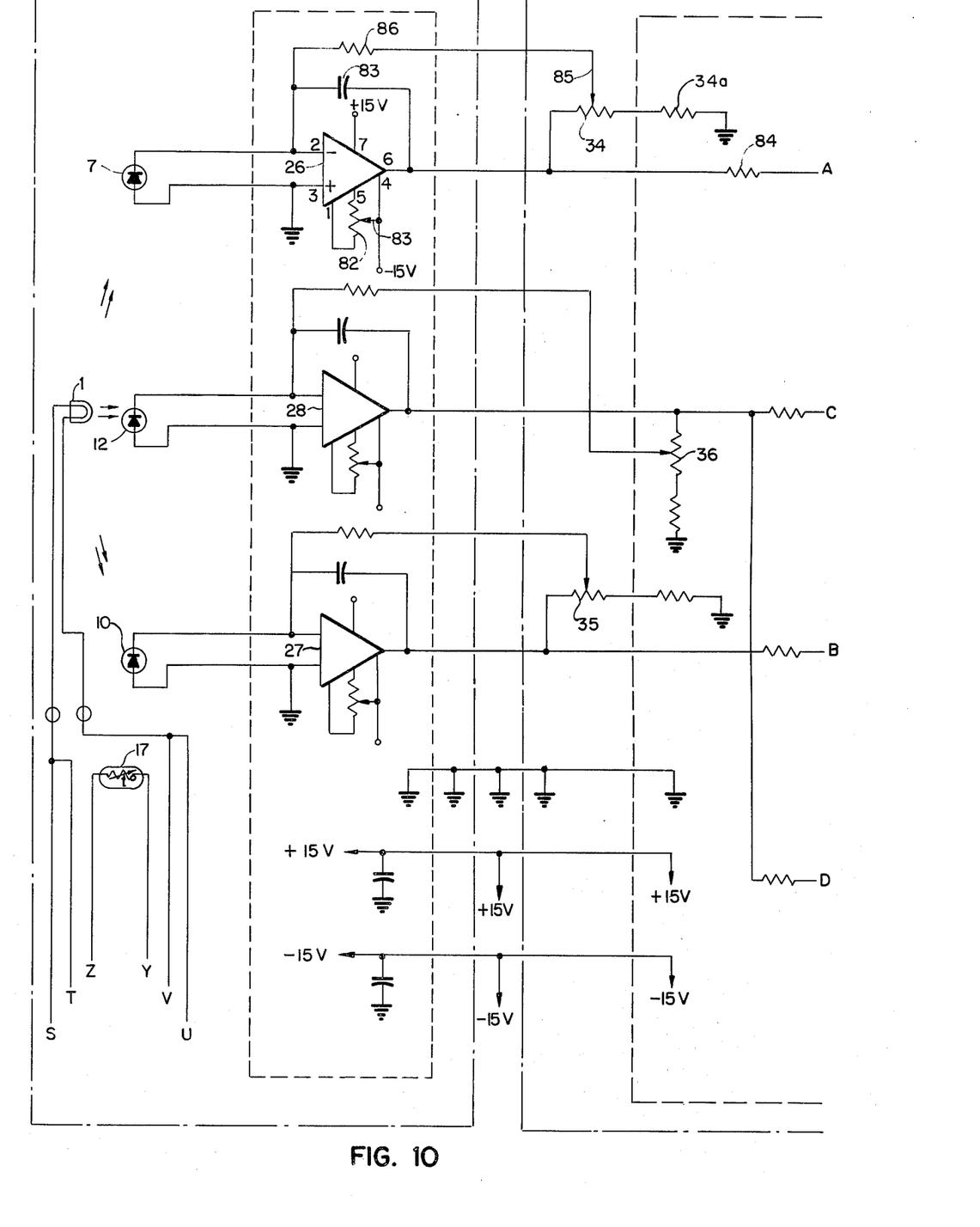

As illustrated in FIGS. 10, the amplifiers 26, 27 and 28 constitute a reamplifier section. Each amplifier may take the form of an integrated circuit such as those sold by Analog Devices under the designation AD504J having a plurality of terminals designated as indicated in FIG. 10. All three amplifiers are connected in the same manner as will be apparent from an explanation of the connections of amplifier 26. In this case the integrated circuit terminals numbered 2 and 3 are connected to the photodiode 7, integrated terminals numbered 7 and 4 are connected respectively to positive and negative 15 volt sources of supply derived from a power supply 81 shown in FIG. 10B. Amplifier offset bias adjustment is provided by potentiometer 82, connected between terminals 1 and 5 of amplifier 26. Offset voltage is derived from the −15 volt supply via wiper 83 of potentiometer 82. Gain adjustment is provided by a voltage divider comprising potentiometer 34 and resistor 34a. This divider network (as shown in FIG. 10) connected between the output (terminal 6) of amplifier 26 and ground, provides an adjustable voltage at the wiper 85 of potentiometer 34 which is connected by feedback resistor 86 to the inverting input (terminal 2) of amplifier 26. Capacitor 83 is connected in the conventional manner across the feedback network to provide noise filtering. Output terminal number 6 of the amplifier 26 is connected through a resistor 84 to the inverting input terminal A of the converting means (see logarithmic amplifier 31a shown in FIG. 10A). The same connections are provided for the amplifiers 27 and 28 as for the amplifier 26. In the case of the amplifier 28 the connections are also the same, although if desired the gain control potentiometer 36 may be mounted within the converting means 31 and 32 (see FIG. 2) instead of externally.

For simplicity the converting means 31 and 32 are shown as block diagrams in the schematic of FIG. 2. However, in FIG. 10A, converting means 31 comprises the amplifier 31a, amplifier 31b and dual transistors operational network 105. Similarly amplifier 32 (of FIG. 2) corresponds in FIG. 10A to amplifier 32a, amplifier 32b and transistors or operational network 106.

The connections to the logarithmic amplifiers 31a and 32a are such as illustrated in greater detail in connection with logarithmic amplifier 31a. The logarithmic amplifiers may comprise one half of an integrated circuit sold under the trade designation IC747. The other half is employed for the amplifier 31b which has integrated circuit terminals 7, 6 10 and 9 brought out corresponding to the terminals numbered 1, 2, 12 and 13 of the integrated circuit 31a and has a negative 15 volt power supply terminal number 4 brought out. The amplifier 31a has a capacitive feedback connection comprising the capacitor 87.

In FIG. 10A, converting means 31 including amplifiers 31a and 31b plus operational network 105 are so interconnected as to provide the operational function required, plus the required signal ranging and temperature compensation. Similarly the interconnections for converting means 32 including amplifiers 32a, 32b, and network 106 are idential to those between amplifiers 31a, 31b and network 105; hence the latter are detailed in FIG. 10A and will be described.

Amplifiers 31a and 31b may comprise two halves of an integrated circuit package sold under the trade designation of IC747 having pin connections designated as shown in FIG. 10A. In FIG. 10A, transistor 101 is the feedback element for amplifier 31a, and transistor 91 is the feedback element for amplifier 31b. Overall gain adjustment plus temperature compensation is provided by returning the base of transistor 91 to point 95 in the voltage divider network comprising resistors 96, 97, and 98, plus thermistor 99.

The physical package of feedback network 105 comprises transistor pair 91 and 101 plus thermistor 99 mounted in thermal contact with transistors 91 and 101. Capacitors 87 and 88 are connected across amplifiers 31a and 31b to provide noise filtering. Resistors 89, 96, 97, and 98 are selected so as to provide a net output of 1 volt per decade; i.e. O.D. is zero volts and 2 O.D. is 2 volts. Subsequent circuitry and recorder ranges are selected to give a maximum span of 0 to 2 O.D. units.

The summing amplifier 39 is shown as having its noninverting input terminal connected through resistors 107 and 108 to the output terminals of the amplifiers 31a and 32a respectively. The amplifier 39 may take the form of an integrated circuit such as those sold under the trade designation 741 having terminal designations as shown in FIG. 10A. As shown, amplifier 39 is connected as a noninverting summing amplifier. Resistors 109 and 110 comprise a feedback network with values selected to set unit gain for this stage.

The ranging and channel selection unit 38 of FIG. 2 comprises, as shown in FIG. 10A, a pair of selector switches 111 and 112 plus two range selector switches 113 and 114. The selector switch 111 comprises a movable contact 115 and three stationary contacts 116, 117 and 118. The stationary contacts 116, 117 and 118 are connected respectively to the output terminals of the 440 millimicron logarithmic amplifier 31a, the summing amplifier 39 and the 570 millimicron logarithmic amplifier 32a to provide signal selection to the first channel of the recorder output 37. The switch 112 has similar connections for the second channel of the recorder output 37.

For range adjustor 113 comprises a range adjustor switch 123 for connection to taps on the voltage divider resistor 122. The arrangement is such that the output terminal 124 to the number 1 channel of a two pen recorder may be connected to various taps on the voltage divider resistor 122 for different scale ranges. For example, in the embodiment illustrated the switch 123 has a movable contact 125 connected to the terminal 124 adapted to make connection with any one of a plurality of stationary taps 126, 127, 128, 129 and 130 to provide a full scale of 0.1, 0.2, 0.5, 1.0, and 2.0 absorbance units or optical density. To provide the ratios between the full scale values suggested by way of example, suitable resistance ratios are provided in the portions of the resistor 122 between the successive taps. Thus, for example, if 2,000 ohms is chosen as the resistance between taps 126 and 127, then the total resistance would be 4,000 ohms with 1,200 ohms between taps 127 and 128, 400 ohms between taps 128 and 129, 200 ohms between taps 129 and 130 and 200 ohms again between tap 130 and the ground connection. Similar connections are provided for the second channel range adjustor 114.

The amplifier 39 may be one of the type known by the trade designation IC741C.

As illustrated in FIG. 10B, power for energizing the lamp 1 may be obtained from a conventional power supply comprising a full wave rectifier 132 connected to 110 volt terminals 133 through a transformer 134. However, voltage regulator 135 is provided with connections through a power amplifier transistors 136 to the full wave rectifier 132 and temperature responsive control connections to the thermistor 17 shown in FIG. 6. As shown the voltage regulator 135 is in the form of an integrated circuit such as sold under the trade designation TCA723 having integrated circuit terminals brought out numbered as follows: 5, 6, 3, 4, 12, 11, 2, 10, 13, and 7. A voltage divider resistor 137 is connected between the integrated circuit terminal numbers 6 and 7 of the voltage regulator 135 with an adjustable tap 138 to the integrated circuit terminal 5. The transistor 17 is connected between the integrated circuit terminal 6 and the tap 139 of the resistor 137. Essentially load current to lamp 1, regulated by power transistor 136, flows through lines U and S in FIG. 10B. The lines V and T are connected to lines U and S at the lamp filament, and provided the load voltage sensing input to regulator 135 (terminal 3, 4, and 7).

The lamp 1 is connected on one side through a resistor 141 to the integrated circuit terminals numbered 2 and 10 of the voltage regulator 135 and on the other side of the integrated circuit terminal number 7 of the amplifier 135.

The power transistor 136 is connected between the integrated circuit terminals numbered 12 and 10 of the voltage regulator 135 with its base connected through the integrated circuit terminal number 11 of the amplifier 135 and a resistor 142 is connected between the omitter and base of the transistor 136. The terminals numbered 3 and 4 of the amplifier 135 are also connected to the lamp 1 through a direct connection 143.

The thermistor 17 is so connected in the control circuits of the voltage regulator 135 that with increasing temperature of the lamp housing 42 to which the thermistor 17 is attached the voltage output from the regulator 135 to the lamp 1 is increased to compensate for the fact that luminous output of the lamp 1 falls with increasing ambient temperature. As seen in FIG. 10B, voltage reference for the power supply is derived within regulator 135 and appears across terminals 6 and 7. This reference is impressed across the network comprising thermistor 17 (connected to Y and Z in FIG. 10B) and the voltage divider comprising the potentiometer 138 and resistors identified generally by the reference numeral 137. The wiper of the potentiometer 138 is connected as an adjustable reference input to regulator 135 and serves as the means to adjust the output signal of the regulator (terminal 11). Thermistor 17 is in series with resistor 144, and connected across the resistor network 137 serves to modify the reference voltage appearing at terminal 5 by causing it to increase slightly as the temperature of thermistor 17 (mounted in thermal contact with the lamp 1) increases.

It is apparent that the present invention provides colorimetric analysis which is substantially free from base line noise effects and provides simultaneous outputs at various wavelengths. It also permits the use of automatic integrators at high degrees of sensitivity and permits analysis of small volume samples. Although particular components, structure and form have been discussed in connection with a specific embodiment of a color-responsive photometer constructed in accordance with the teachings of the present invention, others may be utilized. Furthermore, it will be understood that although an exemplary embodiment of the present invention has been disclosed and discussed, other applications and circuit arrangements are possible and that the embodiments disclosed may be subjected to various changes, modifications and substitutions without necessarily departing from the invention.

What is claimed is:

1. A colorimeter responsive to color properties of a fluid comprising:
   a cuvette;
   means for flowing a fluid through the cuvette and projecting a light beam through the cuvette and the fluid to be analyzed along a first path;
   detector means responsive to the energy of the light beam;
   converting means comprising logarithmic amplifier means connected to said detector means;
   a first dichroic beam separator interposed after said cuvette in said first path for deflecting light below a first selected wavelength in a second beam along a second path and transmitting light above said selected wavelength along said first path;
   a second dichroic beam separator interposed after said first beam separator in said first path for deflecting light below a second selected wavelength in a third beam along a third path and transmitting the remaining light above said second selected wavelength along said first path;
   the detector means comprising detectors interposed in each of said first, second and third paths responsive to the energy of the light beams therein for producing first, second, and third electrical output signals corresponding to the intensity of the energy of light in said first, second and third paths; and
   said converting means being connected to receive said signals from said first and third detectors and from said first and second detectors, said converting means comprising logarithmic operational amplifiers whereby the signals representing transmittance of light are converted into signals proportional to absorbance at the wavelengths in question to produce electrical output signals representative of the difference of the optical absorbances within said cuvette of light between said third beam and said first beam and of the optical absorbances within said cuvette of light between said second beam and said first beam.

2. A colorimeter as described in claim 1 wherein a source of polychromatic light is provided with means for projecting such light through a sample to be analyzed to produce the beam along the first path.

3. A colorimeter as described in claim 2 wherein interposed filters are interposed in the first, second and third light paths, each filter being designed to pass light of predetermined wavelengths with a relatively narrow pass band centered on a wavelength differing from the band of either of the other two filters.

4. A colorimeter as described in claim 3 wherein photodetectors are provided each mounted in one of the light paths beyond the interference filter therein, means are provided for producing signals proportional to the outputs of said photodetectors with means for opposing the signal from the detector in the first light path to the signals from the photodetectors in the second and third light paths.

5. A colorimeter as described in claim 1 wherein said converting means includes a summation amplifier for summing the signals from said logarithmic amplifiers.

6. A colorimeter as described in claim 3 wherein the pass band for the filter in the first light path corresponds to a wavelength higher than the principle absorbing wavelengths in characteristic optical absorption curves for amino acid-ninhydrin reaction products, and the pass band wavelengths of the filters in the second and third light paths are in the regions in which the characteristic optical curves for amino acid-ninhydrin reaction products tend to peak.

7. A colorimeter as described in claim 6 in which the filter in the second light path has a pass band centered on approximately 440 millimicrons (m$\mu$), the filter in the third light path has a pass band centered in approximately 570 millimicrons (m$\mu$) and the filter in the first light path has a pass band centered on approximately 690 millimicrons (m$\mu$).

8. A colorimeter as described in claim 1 wherein the logarithmic operational amplifier responsive to the signal from the photodetector in the first light path has an output applied in opposition to the output of the logarithmic amplifiers responsive to the photodetectors for the second and third light paths.

9. A colorimeter as described in claim 1 wherein an adder is provided having inputs from the logarithmic operational amplifiers responsive to the photodetectors in the second and third light paths.

10. A colorimeter as described in claim 1 wherein a light source for the beam is provided which has a controlled power input responsive to variations in temperature of the light source to maintain the light output from the light source constant.

11. A colorimeter as described in claim 10 wherein the light source is mounted in a housing, a temperature sensing device is mounted on the housing responsive to temperature thereof and the power input of the light source has a control circuit responsive to said temperature sensing device to vary the power input to said light source in accordance with variations of the temperature of the light source housing.

12. A colorimeter as described in claim 1 wherein a cuvette is mounted in the first light path for receiving a liquid to be analyzed and a fluid circuit is provided for supplying liquid to be analyzed to said cuvette.

13. A colorimeter as described in claim 12 wherein an optical head is provided containing the cuvette and the light beam separators and a portion of the fluid circuit is lagged to said optical head for accomplishing substantial uniformity of temperature of the fluid sample and the optical head.

14. A colorimeter as described in claim 1 wherein the light beam separators comprise dichroic mirrors, each having a coating which reflects a large portion of the light beam for wavelengths up to a predetermined limit and transmits the remainder of the light beam.

15. A cuvette holder for use in the measurement of fluid properties comprising a cylinder having a coaxial bore, a substantially radial bore at one end of the axial bore and a second substantially radial bore at the opposite end of the axial bore whereby a cuvette extending longitudinally and having transverse openings at the ends may be mounted in the axial bore and have fluid connections brought through the radial bores in said cylinder, wherein the improvement comprises sealing means in each radial bore for forming fluid tight junctures with the transverse openings of the cuvette, said sealing means each including a packing nut having an inner end;
   a ferrule fitting against said inner end of said packing nut and having a bore countersunk at the inner end of the ferrule;
   a tube extending through said packing nut and said ferrule with a flared inner end;
   a connector fitting with a collar intermediate the ends of the connector fitting;

said connector fitting having a conical outer end and said radial bore in the cuvette holder being counterbored to receive said connector fitting, whereby said packing nut is adapted to clamp said flared end of said tube between said countersunk ferrule bore and said connector fitting outer end, and said connector includes an O-ring at its end opposite said conical end, said O-ring abutting said cuvette to form a fluid tight junction with a transverse opening of said cuvette.

16. In combination, a cuvette holder as described in claim 15 and a cuvette mounted in the axial bore of the cuvette holder, said cuvette having a longitudinal portion composed of tubular member extending coaxially with the axial bore of the cuvette holder and a pair of transverse passages at the opposite ends of the longitudinal portion of said tubular member communicating therewith, each passage extending in the direction of one of the radial bores of the cuvette holder, said cuvette having flat-ground surfaces surrounding the outer ends of each passage with an O-ring interposed between each such flat ground surface and the inner end of a connector fitting.

17. A combination as described in claim 15 wherein means are provided for mounting the cuvette holder coaxially with the line of sight of apparatus for measuring optical properties of fluids.

18. Apparatus for measuring optical properties of a fluid having an optical line of sight from a light source to a light responsive element comprising:
 a cuvette for receiving fluid the properties of which are to be measured, said cuvette including an elongated chamber extending along said optical line of sight;
 an optical head surrounding said line of sight and said cuvette;
 a fluid circuit for supplying fluid sample to said cuvette, said fluid circuit including a coil of tubing in thermal relation to said optical head, said cuvette and coil positioned in close proximity to each other so that the liquid in the cuvette and the optical head are brought into thermal equilibrium.

19. The apparatus described in claim 18 wherein a housing is provided for the light source, a temperature responsive device is mounted in thermal relation to said housing, and a power source is provided for said light source with a regulator responsive to said temperature responsive device for regulating the power input to the light source in response to variations in temperature of the housing.

20. A colorimeter for analyzing the absorbance of a fluid flowing through a cuvette comprising:
 a cuvette;
 means for flowing a fluid through the cuvette and projecting a light beam through the cuvette and the fluid to be analyzed along a first path;
 a first dichroic beam separator interposed after said cuvette in said first path for transmitting a portion of the light in said first path along said first path and for deflecting the remainder of the light in said first path, said dichroic beam separator acting selectively to transmit or deflect light of a wavelength above or below a first selected wavelength, the deflected light being in a second beam along a second path;
 a second dichroic beam separator in one of said light beam paths, said second dichroic beam separator acting selectively for transmitting a portion of the light along the path in which it is located and deflecting the remaining light in a beam along a third path, the second dichroic separator acting selectively with respect to transmission and deflection of light according to whether light in the path in which the second dichroic separator is located is of a wavelength above or below a second selected wavelength;
 first, second and third detector means positioned respectively in each of said first, second and third light paths responsive to energy of said light beams; and
 converting means including logarithmic amplifier means connected to receive output signals from said first, second and third detectors representing transmittance of light through said cuvette and converting said signals into signals proportional to absorbance, said logarithmic amplifier means producing output signals representing the difference between the optical absorbances within said cuvette of light in the highest selective wavelength from the optical absorbances of light in the lower selected wavelengths.

* * * * *